United States Patent
Reavill

(10) Patent No.: US 9,925,356 B2
(45) Date of Patent: *Mar. 27, 2018

(54) LONG CATHETER INFUSION INSERTION METHOD AND APPARATUS

(76) Inventor: Matthew Dickson Reavill, Plainfield, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/560,419

(22) Filed: Jul. 27, 2012

(65) Prior Publication Data

US 2012/0296314 A1   Nov. 22, 2012

Related U.S. Application Data

(63) Continuation of application No. 11/627,857, filed on Jan. 26, 2007, now Pat. No. 8,231,601.

(51) Int. Cl.
   *A61M 25/01* (2006.01)
   *A61M 25/00* (2006.01)

(52) U.S. Cl.
   CPC . *A61M 25/0122* (2013.01); *A61M 2025/0004* (2013.01); *A61M 2025/0175* (2013.01); *A61M 2210/12* (2013.01)

(58) Field of Classification Search
   CPC ...... A61M 2025/0004; A61M 25/0122; A61M 2025/0175; A61M 2210/12
   USPC ............... 604/506, 507, 508, 158, 159, 163, 604/164.01, 164.02, 167.01, 167.03, 604/167.05, 171
   See application file for complete search history.

(56) References Cited

U.S. PATENT DOCUMENTS

| | | | |
|---|---|---|---|
| 3,185,151 A | 5/1965 | Czorny | |
| 3,703,174 A | 11/1972 | Smith | |
| 3,826,256 A | 7/1974 | Smith | |
| 3,903,885 A | 9/1975 | Fuchs | |
| 4,159,022 A | 6/1979 | Pevsner | |
| 4,243,033 A | 1/1981 | DeCaprio et al. | |
| 4,252,122 A * | 2/1981 | Halvorsen | 604/83 |
| 4,304,231 A | 12/1981 | Bodicky et al. | |
| 4,311,139 A * | 1/1982 | Smith | 604/28 |
| 4,326,520 A | 4/1982 | Alley | |
| 4,529,399 A | 7/1985 | Groshong et al. | |
| 4,613,329 A | 9/1986 | Bodicky | |
| 4,906,232 A | 3/1990 | Reynolds | |
| 5,163,903 A | 11/1992 | Crittenden et al. | |
| 5,810,783 A | 9/1998 | Claro | |
| 6,086,008 A | 7/2000 | Gray et al. | |
| 6,517,520 B2 | 2/2003 | Chang et al. | |
| 6,579,484 B1 | 6/2003 | Tiernan et al. | |

(Continued)

*Primary Examiner* — Shefali Patel
(74) *Attorney, Agent, or Firm* — Nixon & Vanderhye P.C.

(57) ABSTRACT

A long catheter can be inserted into a patient while eliminating a need for a sterile field by incorporating the long catheter into an infusion tubing and carrying it in with an infusion. The long catheter has a structure that prevents it from leaving the infusion tubing when fully extended and therefore becomes a connector for fluids to transfer down the long catheter by infusion through the infusion tubing. Use of an adjustable seal connector allows the long catheter to be stopped at varying points during insertion and even to allow the long catheter to be reversed by pulling suction on the infusion tubing and retracting the long catheter back into the infusion tubing. The long catheter also remains within sterile confines of the infusion tubing and therefore is prevented from becoming contaminated.

14 Claims, 4 Drawing Sheets

(56) References Cited

U.S. PATENT DOCUMENTS

| | | |
|---|---|---|
| 6,929,598 B2 | 8/2005 | Kaneko et al. |
| 7,172,580 B2 | 2/2007 | Hruska et al. |
| 2006/0015068 A1 | 1/2006 | Amisar et al. |

* cited by examiner

LONG CATHETER INFUSION INSERTION METHOD AND APPARATUS

CROSS-REFERENCES TO RELATED APPLICATIONS

This application is a continuation of U.S. patent application Ser. No. 11/627,857, filed Jan. 26, 2007, now U.S. Pat. No. 8,231,601, the entire content of which is hereby incorporated by reference in this application.

STATEMENT REGARDING FEDERALLY SPONSORED RESEARCH OR DEVELOPMENT (Not Applicable)

TECHNICAL FIELD

The present invention relates to methods and devices designed for controlling the movement of catheters useful in many medical procedures. In particular, an apparatus and method to facilitate a simple, closed, controlled insertion of a catheter without the need of a guidewire or stylet is disclosed.

BACKGROUND ART

Long catheters are commonly introduced into blood and other vessels during numerous medical procedures. In some procedures, accurate placement within vessels is important and desirable. Generally, guidewires are first inserted into the vessel so that the distal end of the guidewire is at the desired position to be treated. Catheters are provided with a suitable lumen into which the proximal guidewire end is inserted and the catheter is slid over the guidewire or stylet to the desired position.

In addition to difficulties associated with accurate, reproducible catheter placement, handling and manipulation of the catheters in an operating room environment can become unwieldy. Guidewires can create confusion about their use and may be a potential source of contamination during insertion. The need for maintaining sterility and reducing vessel damage during insertion is of concern.

SUMMARY

Of particular emphasis for this product is its ability to let the catheter self insert by utilizing the natural flow of an infusion solution into a vessel, wherein the blood flowing in the vessels continues to carry the catheter. Since this item is entirely contained within a common infusion set, the need for a sterile field and sterile draping has been eliminated.

In an exemplary embodiment, a long infusion catheter is located inside an infusion set. The infusion set is supplied or primed from an infusion source and connected to an introducer catheter that has vessel access within the patient and has a larger inner diameter than the inserting catheter's outer diameter. When the infusion is continued, the flow of the fluid will carry the long infusion catheter into and through the introducer and into the vessel. This continues until a reverse taper or collar of the long infusion catheter at its proximal end becomes lodged at the infusion set's distal end by contact with a luer connector. By trimming excess length of the long infusion catheter at its distal end at the infusion set's distal end prior to connection with the introducer catheter, accurate placement of the catheter within the vessel is assured. Sterility of the inserting catheter is maintained by its complete encapsulation within the infusion set during measurement and insertion.

DESCRIPTION OF EXEMPLARY EMBODIMENTS

Figure 1:
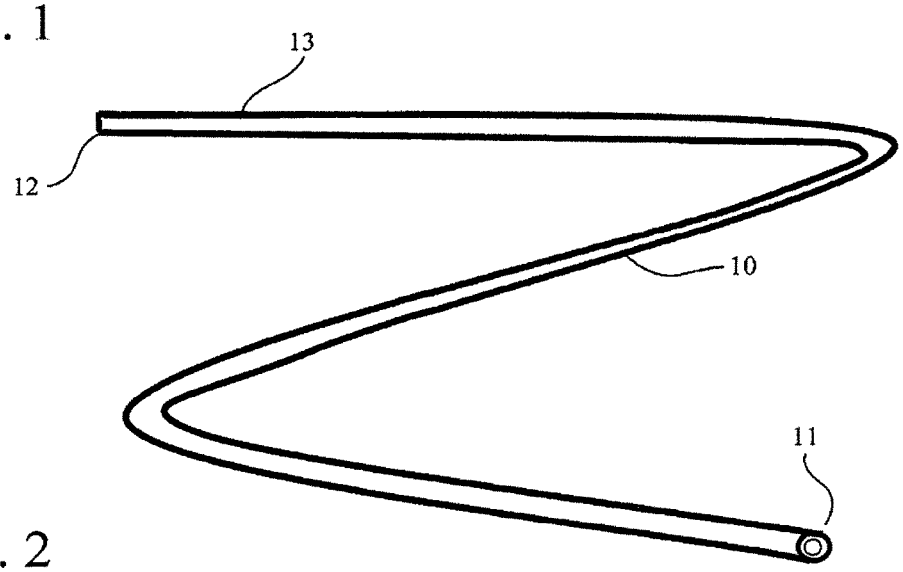
FIG. 1 is a perspective view illustrating a long infusion catheter that has a reverse taper at its proximal end.
Figure 2:
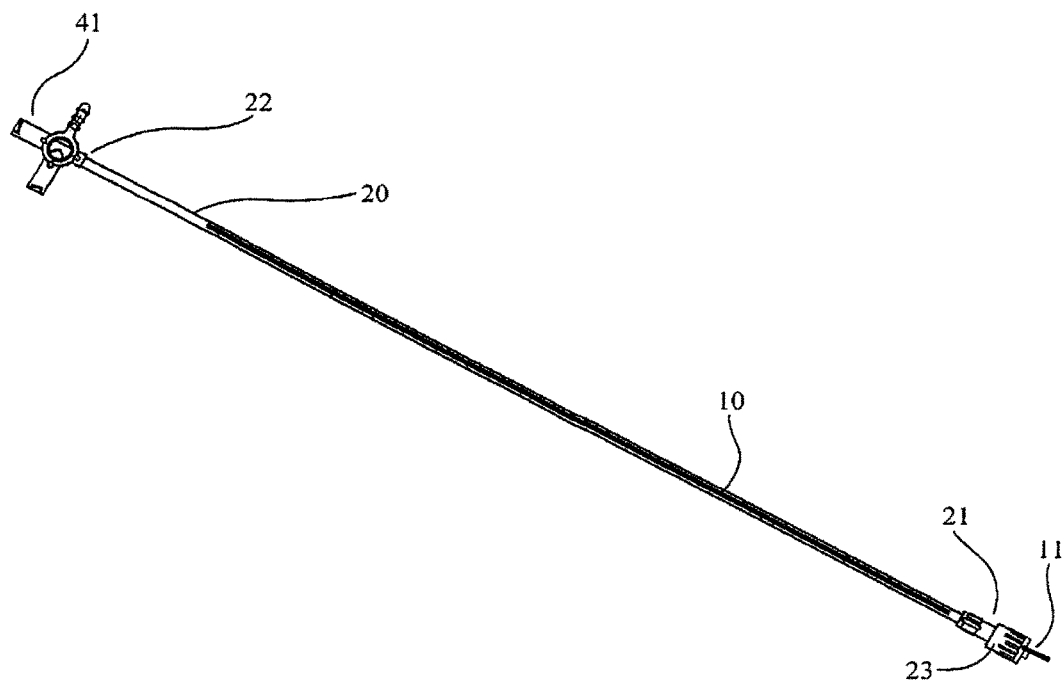
FIG. 2 is a perspective view of a an infusion set with this illustration showing a stop cock at the proximal end and a tubing connector at the distal end and showing the long infusion catheter inside the infusion set.
Figure 3:
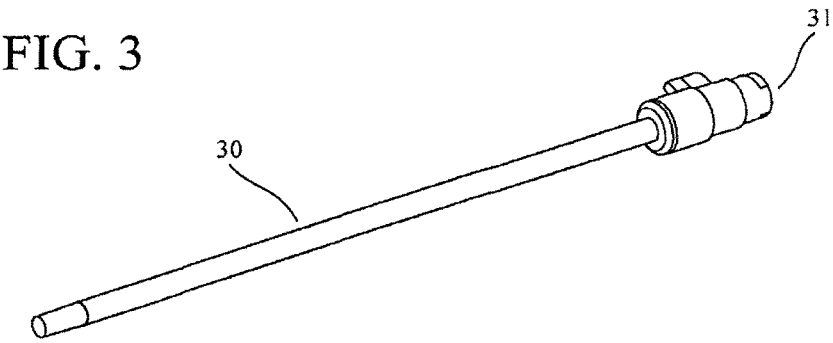
FIG. 3 is a perspective view of a common introducer catheter used to achieve vessel access.
Figure 5:
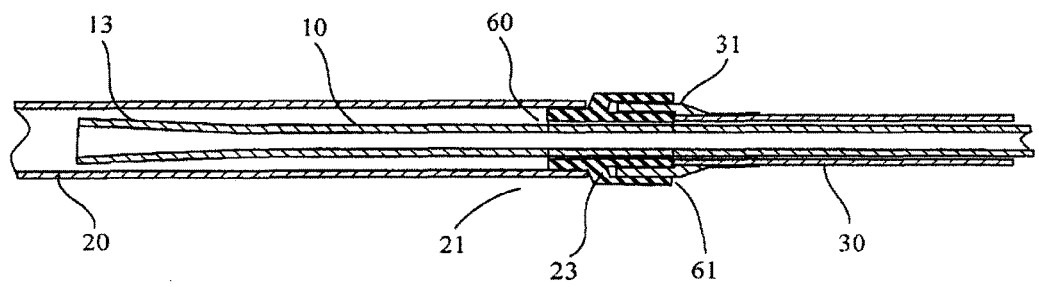
FIG. 5 is cutaway view of one embodiment of the invention connected to the introducer catheter illustrating how the catheter comes to a stop at this connection because a reverse taper portion of the catheter cannot clear the connection.
Figure 6:
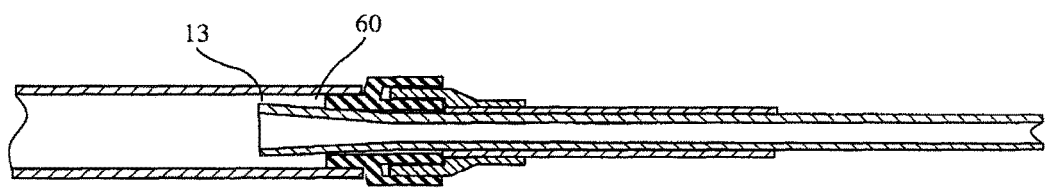
FIG. 6 is cutaway view of one embodiment of the invention connected to the introducer catheter illustrating the proximal end of the long infusion catheter as it is completely advanced.
Figure 7:
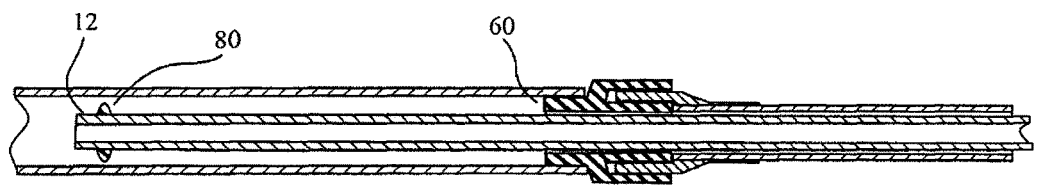
FIG. 7 is cutaway view of one embodiment of the invention where a collar is affixed to the proximal end of the long infusion catheter instead of a reverse taper to prohibit the long catheter from passing beyond the connection.

The apparatus includes a long catheter 10 (FIG. 1), with a distal end 11 and proximal end 12 that has a reverse taper 13 at the proximal end. FIG. 2 shows that this long catheter 10 is within and moves freely within an infusion tubing 20 that is of a larger inner diameter than an outer diameter of the long catheter. The infusion tubing 20 is of similar length to the long catheter and has a matching proximal end 41 and distal end 21 to the long catheter within. The proximal end 41 of the infusion tubing 20 is sealed with a valve 22 at the proximal end 41 and contains a connector 23 at the distal end 21. As shown in FIG. 5, the inner diameter 60 of this connector 23 is larger than the outer diameter of the non reverse tapered portion of the long catheter 10 but smaller than the outer diameter of the reverse tapered portion 13 of the long catheter. These dimensions cause the catheter to form a seal or hang up in the connector and prevent it from escaping the infusion tubing 20 entirely. Fluids that are infused through the valve 22 shown in FIG. 2, at the proximal end 41 of the infusion set 20 carry the long catheter 10 out the connector 23 at the distal end 21. FIG. 7 illustrates that once the reverse tapered proximal end 13 of the long catheter 10 becomes secured within the distal end connector inner diameter 60, the fluid being infused is channeled into the long catheter 10 and not around it as was previous.

Figure 8:
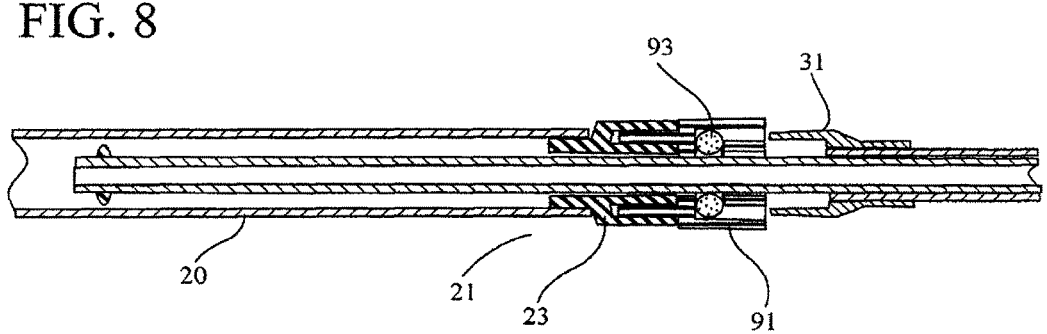
FIG. 8 is cutaway view of one embodiment of the invention where the infusion tubing connector is connected to an adjustable seal connector which is then about to be connected to the introducer catheter.

FIG. 8 illustrates an alternate method of forming a seal and thereby stopping the progress of the long catheter past the connector 23 using a collar 80 or catch on the proximal end 12 of the long catheter 10. Instead of using a reverse taper on the proximal end 12, a collar type device is used that has a wider outer diameter than the inner diameter 60 of the connector. Therefore the catheter can travel through the connector until it reaches the collared point of the long catheter 10 and then forms a seal with the inner diameter of the connector 23.

Figure 4:
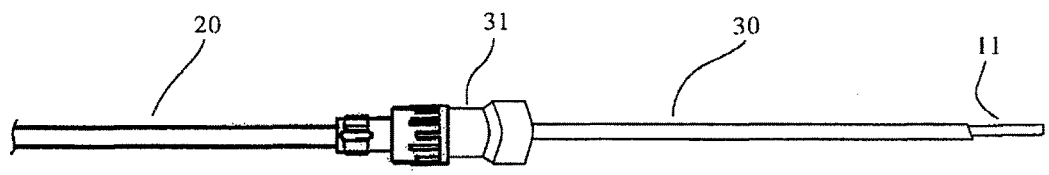
FIG. 4 is a perspective view illustrating one embodiment of the invention connected to the introducer catheter and the distal end of the long infusion catheter as it is propelled forward by the flow of the infusion.

FIG. 4 shows a connection of the infusion tubing 20 with catheter inside to an introducer catheter at the introducer connector 31. The illustration does not show the introducer catheter 30 inside a vessel but that can be implied as a common use of introducer catheters to deliver catheters 11 into the vessel to which they have achieved access. Provided that the introducer has achieved vessel access, the apparatus above will carry the long catheter through the introducer catheter 30 and into the accessed vessel with the fluid being infused. Once the reverse taper 13 meets with the connector 23 and forms a seal, the long catheter 10 becomes the sole conduit of the infusion and migrates no further within the vessel. Additional fluid may be used to propel the long catheter 10 along this path by utilizing syringes with fluid at connection points up stream of the infusion tubing's proximal end 41 illustrated as a stopcock valve 22 in FIG. 2.

Figure 9:
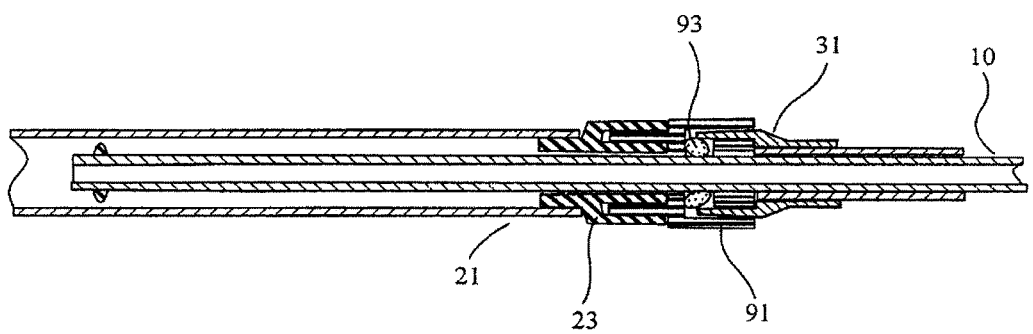
FIG. 9 is cutaway view of one embodiment of the invention where the infusion tubing connector is connected to an adjustable seal connector which is then fully connected to the introducer catheter, creating a braking effect on the catheter.
Figure 10:
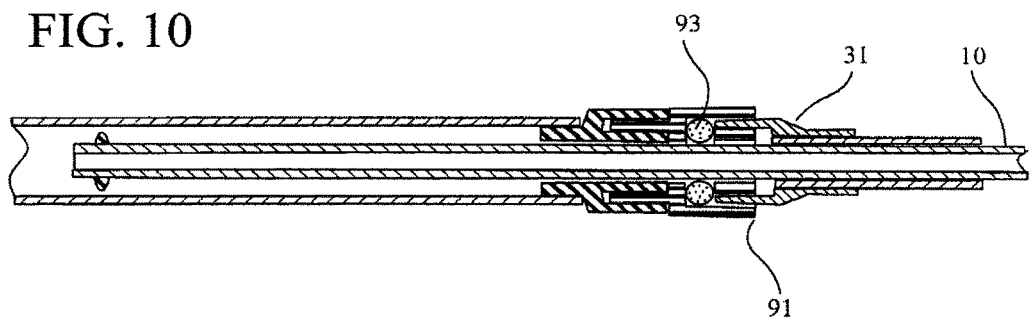
FIG. 10 is cutaway view of one embodiment of the invention where the infusion tubing connector is connected to an adjustable seal connector, which is then partially connected to the introducer catheter to release the braking effect on the catheter of FIG. 9.

FIG. 8 illustrates how an adjustable seal connector 91 may be used between the connections of the distal end connector 23 of the infusion tubing 20 and the connecting end 31 of the introducer catheter 30 to provide intermittent brakes in the insertion. The adjustable seal connector 91 contains an elastic gasket 93 that donuts the long catheter 10. When the adjustable seal connector 91 is fully connected to the introducer, FIG. 9, the elastic gasket 93 becomes compressed, thereby compressing the long catheter 10 and prohibiting its movement. FIG. 10 shows the adjustable seal connector 91 partially connected to the introducer catheter connector 31, wherein the elastic gasket 93 is in its normal state, and the long catheter 10 is allowed to travel within.

These adjustable seals can also facilitate reversing the catheter insertion by allowing only the catheter to return into the infusion set when suction or negative pressure is applied to the proximal end of the catheter. Setting the adjustable seal to allow the catheter only to pass causes the catheter to withdraw into the infusion tubing to relieve the pressure thus traveling in reverse. This method keeps the catheter free of contamination for later reinsertion.

The apparatus and method described herein is more intuitive and facilitates quicker and simpler catheter insertions than present guide wire and sterile drape methods. The advantages of enhanced sterile technique are self apparent. The ability to reverse the catheter and maintain sterility of such before reinsertion will be a vast improvement over current methods that require alternate apparatus and more often disposal to accomplish the same end result. Although exemplary embodiments have been described in detail, additional embodiments exist that remain within the general concept of this invention. The foregoing disclosure, descriptions and figures are only for illustrative purposes and do not, in any way, limit the invention which is defined by the following claims.

The invention claimed is:

1. A method for inserting a long catheter comprising:
securing an introducer catheter in a vessel, the introducer catheter including a connector attached thereto;
attaching a length of infusion tubing at a distal end to the connector, a proximal end of the infusion tubing including a valve;
inserting the long catheter into the infusion tubing, the long catheter including a sealing assembly; and
infusing the long catheter by flowing fluid through the infusion tubing and through and around the long catheter until the long catheter is positioned through the introducer catheter such that the sealing assembly forms a seal with the connector, wherein the infusing step is practiced such that when sealed with the connector, the sealing assembly of the long catheter directly engages an outermost upstream side of the connector.

2. The method as set forth in claim 1, wherein the sealing assembly comprises a reverse taper on a sealing end of the long catheter and wherein the infusing step comprises flowing the fluid through the infusion tubing until the sealing end of the long catheter engages the connector.

3. The method as set forth in claim 1, wherein the sealing assembly comprises a collar on a sealing end of the long catheter, and wherein the infusing step comprises flowing the fluid through the infusion tubing until the collar of the long catheter engages the connector.

4. The method as set forth in claim 1, further comprising stopping the long catheter intermittently by use of a variable compression seal to act as a brake.

5. The method as set forth in claim 1, further comprising reversing the insertion or retracting the inserted long catheter by applying a negative pressure to the infusion tubing causing the long catheter to retract.

6. The method as set forth in claim 1, wherein the step of attaching the length of infusion tubing at the distal end to the connector is practiced by attaching the length of infusion tubing at the distal end directly to the connector.

7. The method as set forth in claim 6, wherein the infusing step is practiced by infusing the long catheter such that the sealing assembly forms the seal directly with the connector.

8. An apparatus for inserting and advancing a long catheter, the apparatus comprising:
a length of infusion tubing with a valve on a proximal end and a connector on a distal end, the distal end of the infusion tubing being directly coupled with the connector, the infusion tubing consisting of a continuous, one-piece tubing;
the long catheter whose outer diameter is less than an inner diameter of the infusion tubing connector, the long catheter including a sealing assembly that forms a seal with the connector when the catheter is fully extended, wherein the infusion tubing, the connector and the long catheter are configured such that at least a portion of the long catheter is disposed in the infusion tubing when the catheter is fully extended, and wherein the long catheter is substantially the same length as the infusion tubing such that substantially an entire length of the long catheter is simultaneously movable within the length of infusion tubing;
an introducer catheter with an inner diameter large enough to allow the long catheter to pass within, the introducer catheter being connectable to the infusion tubing at the connector, wherein at least a portion of the introducer catheter is concentric with at least a portion of the connector; and an infusion source cooperable with the infusion tubing valve.

9. The apparatus of claim 8, wherein the sealing assembly comprises a collar at a trailing end of the long catheter to stop the long catheter from moving beyond the connector and form the seal.

10. The apparatus of claim 8, further comprising a variable seal gasket connected between the infusion tubing connector and the introducer catheter that allows progression of the long catheter to be halted or restarted.

11. The apparatus of claim 8, wherein the sealing assembly comprises a reverse taper on a trailing end of the long catheter, the reverse taper sealingly engaging the connector in a fully extended position.

12. An apparatus for inserting and advancing a long catheter cooperable with an introducer catheter, the apparatus comprising:
a length of infusion tubing with a valve on a proximal end and a connector on a distal end, the distal end of the infusion tubing being directly coupled with the connector;
the long catheter whose outer diameter is less than an inner diameter of the infusion tubing connector, the long catheter including a sealing assembly that forms a direct seal with an outermost upstream side of the connector when the long catheter is fully extended such that at least a portion of the long catheter is disposed in the infusion tubing when the long catheter is fully extended, wherein the long catheter is substantially the same length as the infusion tubing such that substantially an entire length of the long catheter is simultaneously movable within the length of infusion tubing; and
an infusion source cooperable with the infusion tubing valve, the infusion source being operable to flow fluid through and around the long catheter and through the infusion tubing to infuse the long catheter.

13. The apparatus of claim 12, wherein the sealing assembly comprises a reverse taper on a trailing end of the long catheter, the reverse taper sealingly engaging the connector in a fully extended position of the long catheter.

14. The apparatus of claim 12, wherein the sealing assembly comprises a collar secured to a trailing end of the long catheter, the collar sealingly engaging the connector in a fully extended position of the long catheter.

* * * * *